(12) United States Patent
Stoffel et al.

(10) Patent No.: US 6,753,583 B2
(45) Date of Patent: Jun. 22, 2004

(54) ELECTROSTATIC ELECTROACOUSTICAL TRANSDUCER

(75) Inventors: Axel Stoffel, Donaueschingen (DE); Zdenek Skvor, Prag (CZ)

(73) Assignee: Fachhochschule, Furtwangen (DE)

(*) Notice: Subject to any disclaimer, the term of this patent is extended or adjusted under 35 U.S.C. 154(b) by 36 days.

(21) Appl. No.: 10/372,984

(22) Filed: Feb. 24, 2003

(65) Prior Publication Data

US 2003/0151105 A1 Aug. 14, 2003

Related U.S. Application Data

(63) Continuation of application No. PCT/EP01/09766, filed on Aug. 23, 2001.

(30) Foreign Application Priority Data

Aug. 24, 2000 (EP) .............................................. 00118349

(51) Int. Cl.[7] .............................................. H01L 29/82
(52) U.S. Cl. ...................... 257/416; 257/415; 257/417; 257/418
(58) Field of Search ................................ 257/415, 416, 257/417, 418

(56) References Cited

U.S. PATENT DOCUMENTS

| | | | | |
|---|---|---|---|---|
| 3,827,002 A | * | 7/1974 | Chao | 333/193 |
| 4,006,317 A | | 2/1977 | Freeman | |
| 5,930,595 A | * | 7/1999 | Sridhar et al. | 438/52 |
| 6,465,854 B1 | * | 10/2002 | Muenzel et al. | 257/417 |
| 2001/0005032 A1 | * | 6/2001 | Aigner et al. | 257/415 |

FOREIGN PATENT DOCUMENTS

| | | |
|---|---|---|
| DE | 199 00 969 A1 | 8/1999 |
| WO | WO 00/01194 | 1/2000 |

* cited by examiner

Primary Examiner—Ngâm V. Ngô
(74) Attorney, Agent, or Firm—Laurence A. Greenberg; Werner H. Stemer; Ralph E. Locher

(57) ABSTRACT

An electrostatic electroacoustical transducer contains an electrically conductive fixed electrode plate having an active surface with recesses. A conductive or semiconductive flexible diaphragm is disposed at a distance from the active surface of the electrode plate and within the recesses. An insulating device is disposed between the electrode plate and the diaphragm.

11 Claims, 5 Drawing Sheets

ELECTROSTATIC ELECTROACOUSTICAL TRANSDUCER

CROSS-REFERENCE TO RELATED APPLICATIONS

This application is a continuation of copending International Application No. PCT/EP01/09766, filed Aug. 23, 2001, which designated the United States and was published in English.

BACKGROUND OF THE INVENTION

Field of the Invention

The present invention relates to an electrostatic capacitive transducer containing a conductive or semiconductive diaphragm spaced apart from one or more back plate electrodes. The transducer has insulation disposed between the back plate electrode and the diaphragm.

Transducers of the above mentioned kind can be used for electrostatic sensors or electrostatic actuators like receivers or transmitters, in particular microphones or earphones inserted into the auditory canal of an ear. The functional properties of such a transducer, like the sensitivity of the receiver, the emitted power or the sound pressure level of the transmitter highly depend on the effective surface of the diaphragm. However, while a big surface of the diaphragm is desirable, a small overall size and a small volume of the transducer are important, too.

SUMMARY OF THE INVENTION

It is accordingly an object of the invention to provide an electrostatic electroacoustical transducer that overcomes the above-mentioned disadvantages of the prior art devices of this general type, which improves the functional properties of the electrostatic electroacoustical transducer and at the same time does not increase the overall size and the volume of the transducer. In particular it is an object of the present invention to increase the effective surface of the diaphragm of an electrostatic electroacoustical transducer without increasing the size and the volume of the transducer.

With the foregoing and other objects in view there is provided, in accordance with the invention, an electrostatic capacitive transducer. The transducer contains an electrically conductive fixed electrode plate having an active surface with recesses, and a conductive or semiconductive flexible diaphragm disposed at a distance from the active surface of the electrically conductive fixed electrode plate and within the recesses. An insulating device is disposed between the electrically conductive fixed electrode plate and the diaphragm. A device is provided for detecting a capacitance between the electrically conductive fixed electrode plate and the diaphragm.

According to the present invention the diaphragm does not only extends in a horizontal direction but additionally into the recesses on the active surface of the electrode plate in a vertical direction. Irrespective of the extension of the diaphragm, it always vibrates in a normal direction to its orientation. Therefore the present invention leads to a larger effective surface of the diaphragm. At the same time the overall size and the volume of the transducer are not increased. In other words, while the overall size and the volume of the transducer may be maintained about the same, the effective surface of the diaphragm is increased considerably.

The transducer according to the present invention may be used as any kind of capacitive sensor for measuring quantities that influence the capacitance between the electrode plate and the diaphragm of the transducer. For example, the transducer may be used as a pressure sensor for measuring a static pressure, which decreases the distance between the diaphragm and the electrode plate and leads to a change of capacitance. Another example of a preferred use of the transducer is the use as a humidity sensor for measuring the humidity, which leads to a change of capacitance, too. Finally, another example is the use of the transducer as an electroacoustical transducer (receiver or transmitter) for detecting or emitting sound waves. The change of capacitance can be detected with an appropriate electronic circuit known in the state of the art.

According to a preferred embodiment of the present invention, the recesses are configured as parallel trenches disposed on the active surface of the electrode plate. The diaphragm extends within the parallel trenches at a distance from the active surface of the electrode plate, thereby allowing a vibration of the diaphragm and increasing the effective surface of the diaphragm considerably. The deeper the trenches are, the more the effective surface of the diaphragm can be increased.

The trenches may have various cross sectional areas. For example, it is possible, that the trenches have a triangular cross-sectional area with the walls of each trench meeting in a base line. It is also possible to round off the base line. Furthermore, the walls could extend perpendicularly relative to the active surface of the electrode plate.

Preferably the trenches have a rectangular cross sectional area. This allows the maximum increase in effective surface of the diaphragm while maintaining the overall size and the volume of the transducer.

According to another preferred embodiment of the present invention the insulating device is an air gap disposed between the active surface of the electrode plate and the diaphragm. If the transducer is used as a receiver, e.g. as a microphone, the diaphragm is pressed closer to the walls of the recesses and to the active surface of the electrode plate by an acoustic pressure wave. The diaphragm vibrates in a normal direction to the walls of the recesses. The decrease in the distance between the diaphragm and the electrode plate during vibration leads to a change of the capacitance between the electrode plate and the diaphragm. The change of capacitance can be detected with an appropriate electronic circuit known in the state of the art.

If the transducer is used as a transmitter, e.g. a loud speaker, DC-voltage is applied between the active surface of the electrode plate and the diaphragm. With an additional AC-voltage the diaphragm is stimulated and begins to vibrate. The vibrations cause acoustic pressure waves to be emitted by the transducer that cause a sound signal.

According to yet another preferred embodiment of the present invention the recesses contain openings into a back volume of the transducer. The openings are formed at the bottom of the recesses and are covered by the diaphragm. The air gaps are acoustically in communication with the back volume.

Preferably the back volume is delimited by the electrode plate and by a support carrier, which is disposed at a distance from the electrode plate facing a surface of the electrode plate opposite to its active surface. The distance between the support carrier and the surface opposite to the active surface of the electrode plate may for example be achieved by one or more depressions provided on a surface of the support carrier facing the surface of the electrode plate opposite to its active surface. However, this does not exclude, that the support carrier, for example around its edges or around the edges of the depressions, is in contact with the surface of the electrode plate opposite to its active surface.

Preferably, the transducer contains a cover plate disposed opposite to the active surface of the electrode plate and at a distance from the diaphragm. For keeping the cover plate at a desired distance from the diaphragm and the active surface of the electrode plate, spacer elements may be disposed between the electrode plate and the cover plate. The electronic circuit for detecting vibrations of the diaphragm or for stimulating the diaphragm to vibrate may be disposed within these spacer elements.

According to yet another preferred embodiment of the present invention the cover plate is configured as a further electrically conductive fixed electrode plate having an active surface with recesses. A further conductive or semiconductive flexible diaphragm is disposed at a distance from the active surface of the further electrode plate and within the recesses, and a further insulating device is disposed between the further electrode plate and the further diaphragm. Wherein the electrode plate and the further electrode plate are disposed relative to each other in such a way that the diaphragm and the further diaphragm face each other.

According to this embodiment of the present invention the spacer elements are disposed between the electrode plate and the further electrode plate keeping the distance between the diaphragm and the further diaphragm or the active surface of the electrode plate and the active surface of the further electrode plate, respectively. The space between the diaphragm and the further diaphragm forms an acoustical wave guide running into at least one slot. Acoustical waves enter the transducer from outside through the slots run along the acoustical wave guide and stimulate vibration of the diaphragm and of the further diaphragm. Alternatively the diaphragm and the further diaphragm are electronically stimulated in order to generate sound waves that run along the wave guide and leave the transducer through the slots. This principle is described in detail in the U.S. Pat. No. 6,249,586, filed on Jan. 21, 1998 and published on Jun. 19, 2001, which is to be incorporated into the present patent application by reference.

According to the present invention it is possible to stack a plurality of electrode plates, flexible diaphragms, insulating devices and cover plates in such a way that an electrode plate of a first stack layer faces a cover plate of the next stack layer.

Other features which are considered as characteristic for the invention are set forth in the appended claims.

Although the invention is illustrated and described herein as embodied in an electrostatic electroacoustical transducer, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
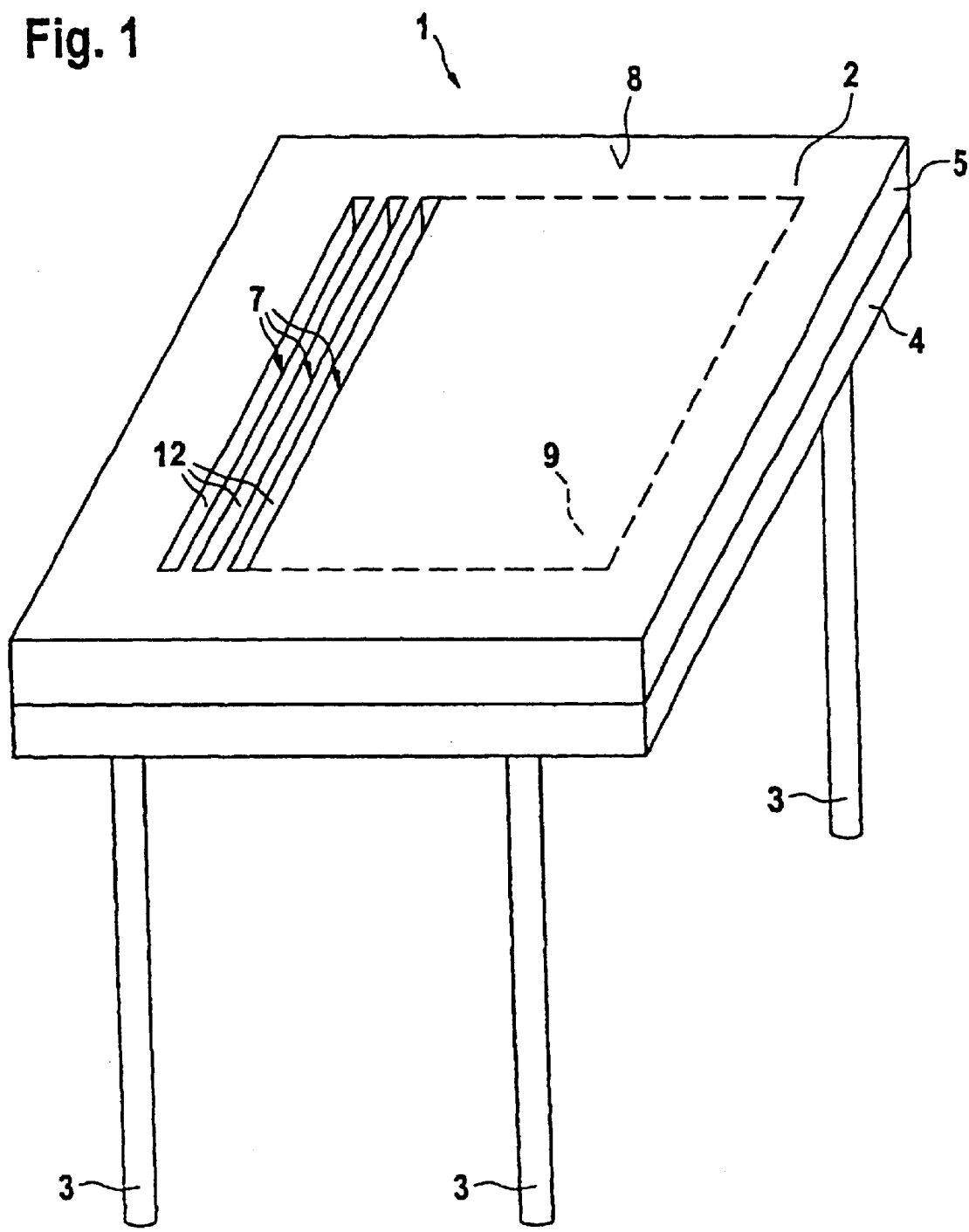
FIG. 1 is a diagrammatic, perspective view of a first preferred embodiment of a transducer according to the invention.

Referring now to the figures of the drawing in detail and first, particularly, to FIG. 1 thereof, there is shown a transducer 1 according to the present invention in its entirety. The transducer 1 contains a transducer chip 2 and electrical contact terminals 3. The transducer 1 is fabricated with a silicon micromachining technology. The transducer chip 2 contains a support carrier 4 and an electrically conductive electrode plate 5.

The support carrier 4 serves for mechanical support. It has a depression on its surface facing the electrode plate 5. The electrode plate 5 is fixed to the support carrier 4 along the edges of a depression forming a back volume (wall) 6 in the inside of the transducer chip 2 (see FIG. 3).

The electrode plate 5 has recesses that are configured as parallel trenches 7. The trenches 7 can be obtained by a deep reactive ion etching (DRIE) method. The DRIE method is well known in the state of the art (see "Reactive-Ion Etching of Smooth Vertical Walls in Silicon", at http://www.nasatech.com/Briefs/Oct00/NPO20756.html; "Reactive Ion Etching", http://www.el.utwente.nl/tdm/mmd/projects/rie/ and "MEMS devices Through Deep Reactive Ion Etching of Single-Crystal Silicon", http://transducers.stanford.edu/stl/Projects/mems.html). The trenches 7 have a rectangular cross sectional area. Of course, the trenches 7 may have cross sectional areas other than rectangular.

Figure 3:
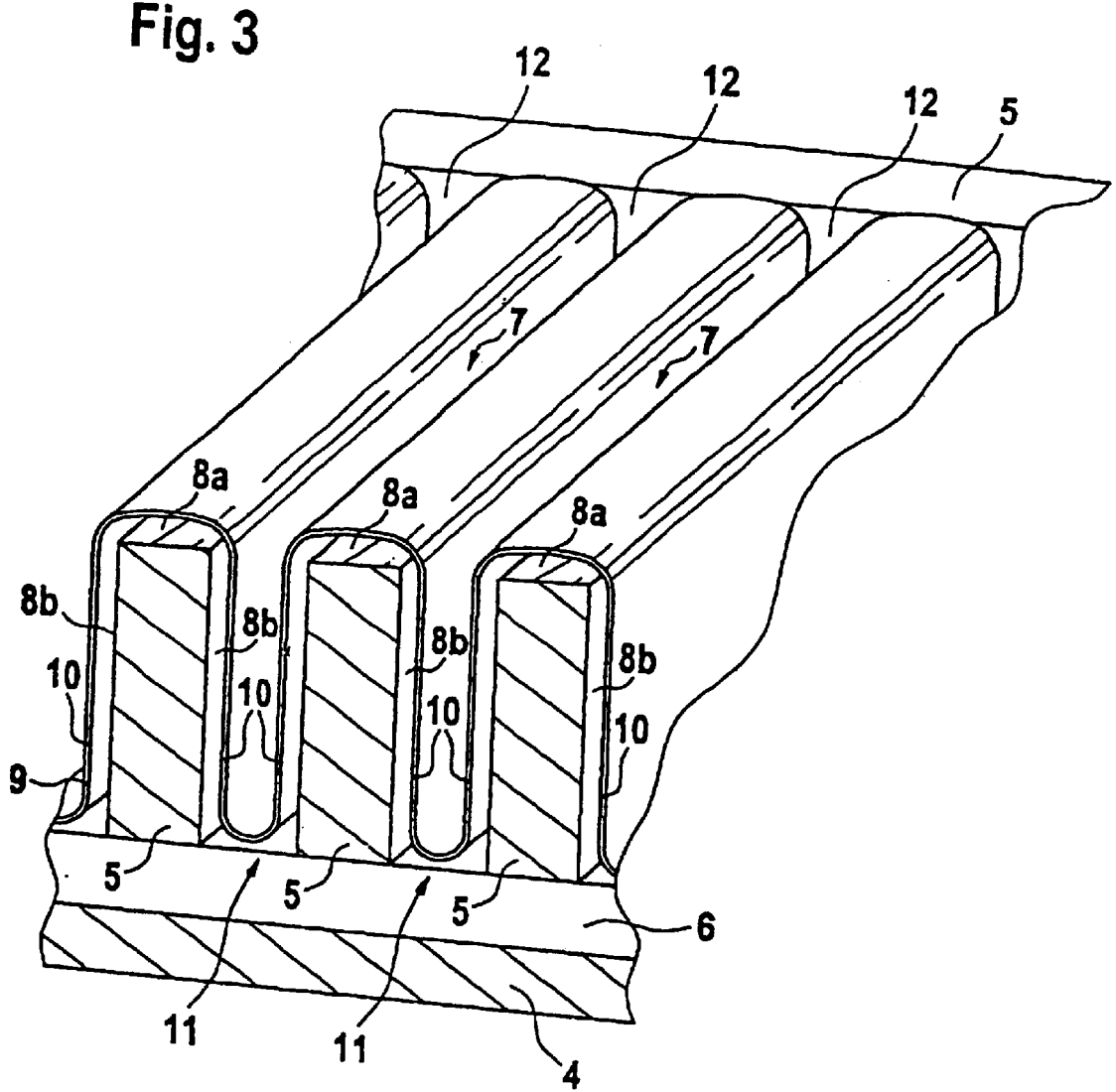
FIG. 3 is a perspective, partial sectional view of the transducer according to FIG. 1.

A top side of the electrode plate 5 shown in FIG. 3 is the so called active surface 8. The active surface 8 contains top walls 8a on top of the electrode plate 5 and side walls 8b delimiting the trenches 7. At the bottom of the trenches 7 there are openings 11 communicating with the back volume 6.

There is a conductive or semiconductive flexible diaphragm 9 disposed at a distance from the active surface 8 of the electrode plate 5 and extending within the trenches 7. The material of the diaphragm 9 may be polysilicon or a laminate layer of polysilicon and silicon nitride. Polysilicon is a semiconductive material that is highly dotated in order to achieve conductivity properties. The diaphragm 9 covers the openings 11.

An electrically insulating device 10 is disposed in a gap between the diaphragm 9 and the active surface 8 of the electrode plate 5. The insulating device 10 is configured as an air gap. The gap can be made with a state of the art sacrificial layer technique using silicon dioxide or polysilicon or by using porous silicon with its high etch rate as a sacrificial layer.

Figure 2:
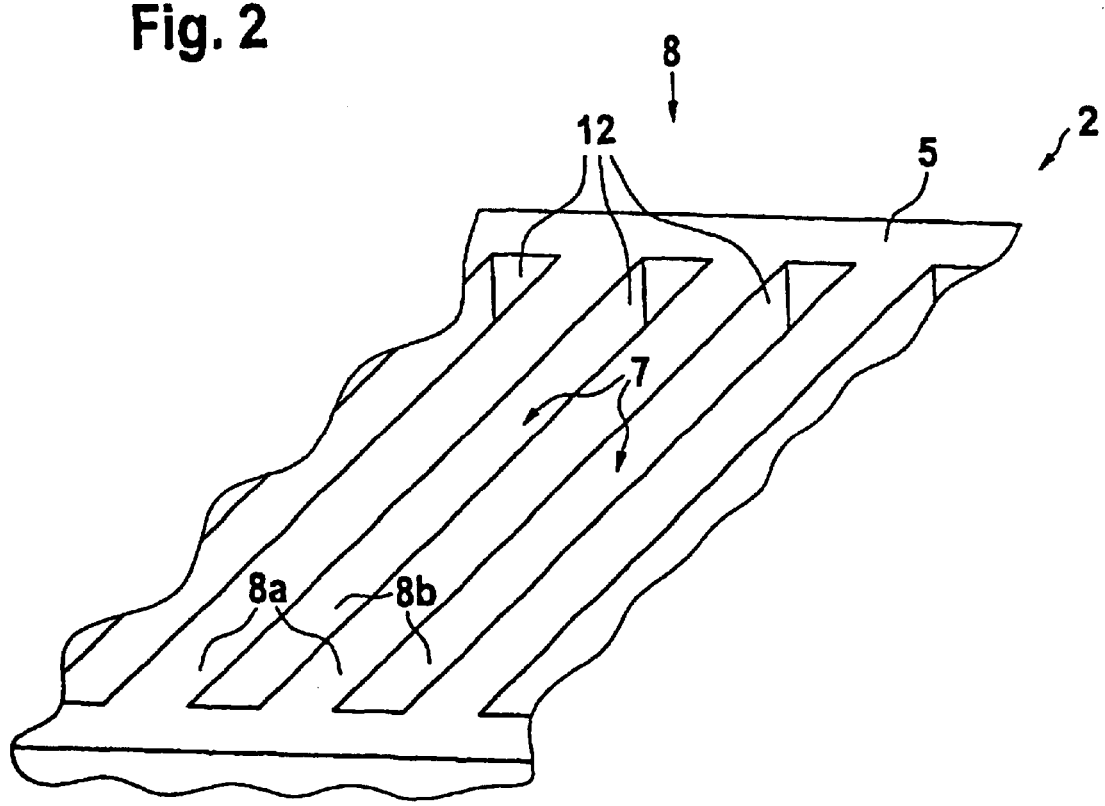
FIG. 2 is an enlarged, partial top perspective view of the transducer according to FIG. 1.

On the top of the transducer chip 2 there are input/output slots 12 for permitting acoustical waves to enter or leave the transducer 1 and to use the transducer 1 as a receiver or as a transmitter. In the embodiment of FIGS. 1 to 3 the slots 12 are constituted as openings at the top of the trenches 7.

The acoustic waves entering the input/output slots 12 provoke an acoustic pressure causing the diaphragm 9 to vibrate. As a consequence a capacitance between the diaphragm 9 and the electrode plate 5 changes. The change of capacitance can be converted into an electrical output signal, for example an output voltage, of the transducer 1. The conversion of the acoustic waves into the output signal may be effected by an appropriate electronic circuit known in the state of the art.

If the transducer 1 is used as a transmitter, an electrical signal, for example an AC-voltage and DC-voltage, is generated and applied to the transducer 1 by the terminals 3. The DC-voltage charges the capacitor formed by the diaphragm 9 and the active surface 8 of the electrode plate 5. The superimposed AC-voltage causes the diaphragm 9 to vibrate and therefore emitting acoustic waves. The acoustic waves leave the transducer 1 through the input/output slots 12 causing an acoustic signal. The transducer 1 shown in the figures is a single-acting transducer, which results in that the movement of the diaphragm 9 is stimulated only into one direction. The movement into the opposite direction is caused by the resiliency of the material of the diaphragm 9 after the stimulation is no longer active. However, it is possible to configure the transducer 1 according to the present invention as a double-acting transducer, too. This would require a further electrode plate extending into the trenches 7, the diaphragm 9 being enclosed between the electrode plate 5 (stimulating the movement of the diaphragm 9 into the first direction) and the further electrode plate (stimulating the movement into the opposite direction).

Figure 4:
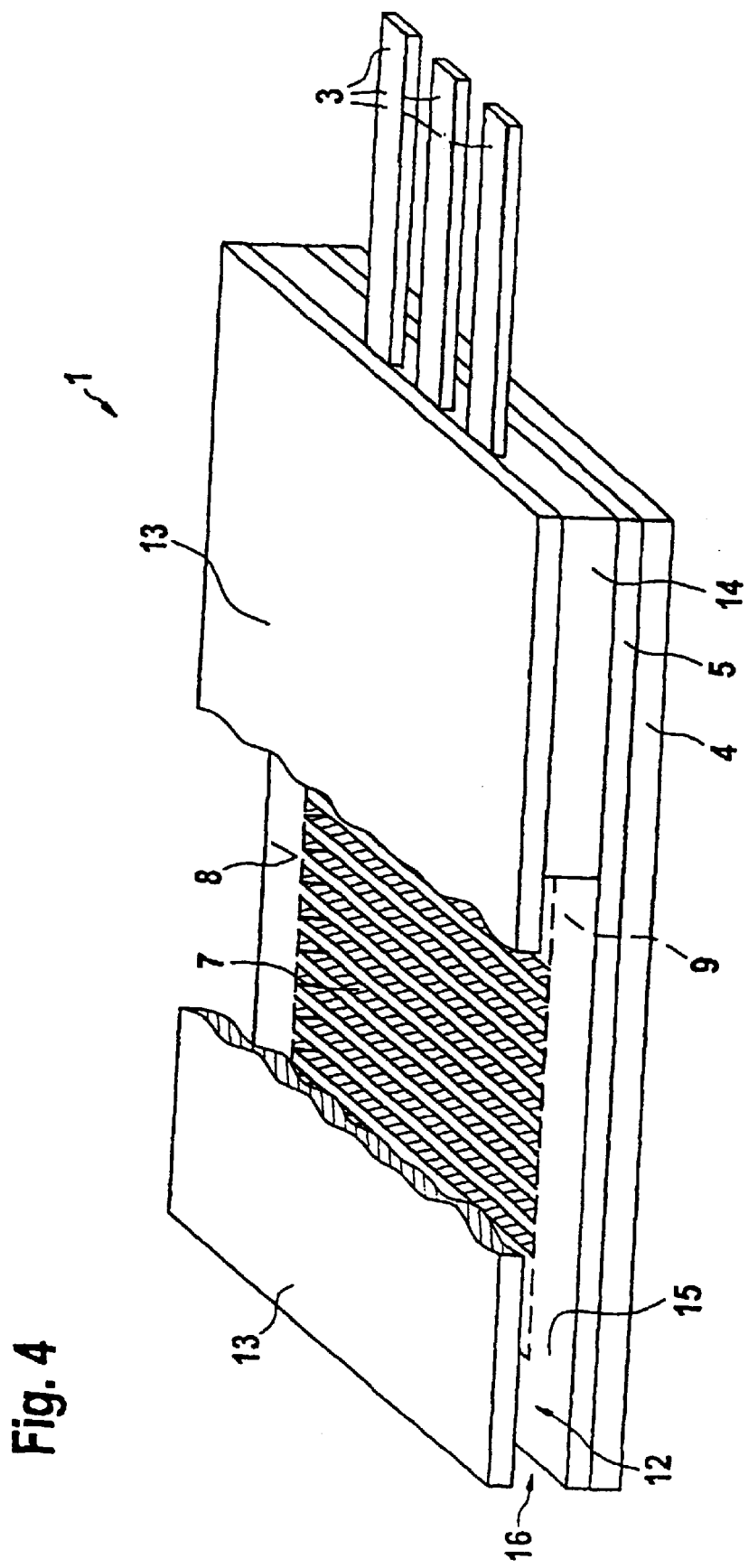
FIG. 4 is a perspective, partially cut-away view of a second preferred embodiment of the transducer according to the present invention.

In FIG. 4 a second embodiment of the transducer 1 according to the present invention is shown. It contains a cover plate 13 disposed above the active surface 8 of the electrode plate 5 and at a distance from the diaphragm 9. There is a spacer element 14 disposed between the electrode plate 5 and the cover plate 13 in order to maintain the distance between the cover plate 13 and the electrode plate 5. An electronic circuit for detecting vibrations of the diaphragm 9 or for stimulating the diaphragm 9 to vibrate may be disposed within the spacer element 14. In the embodiment of FIG. 4 the input/output slots 12 communicate with openings 15 to the side and an opening 16 at the front of the transducer 1.

Figure 5:
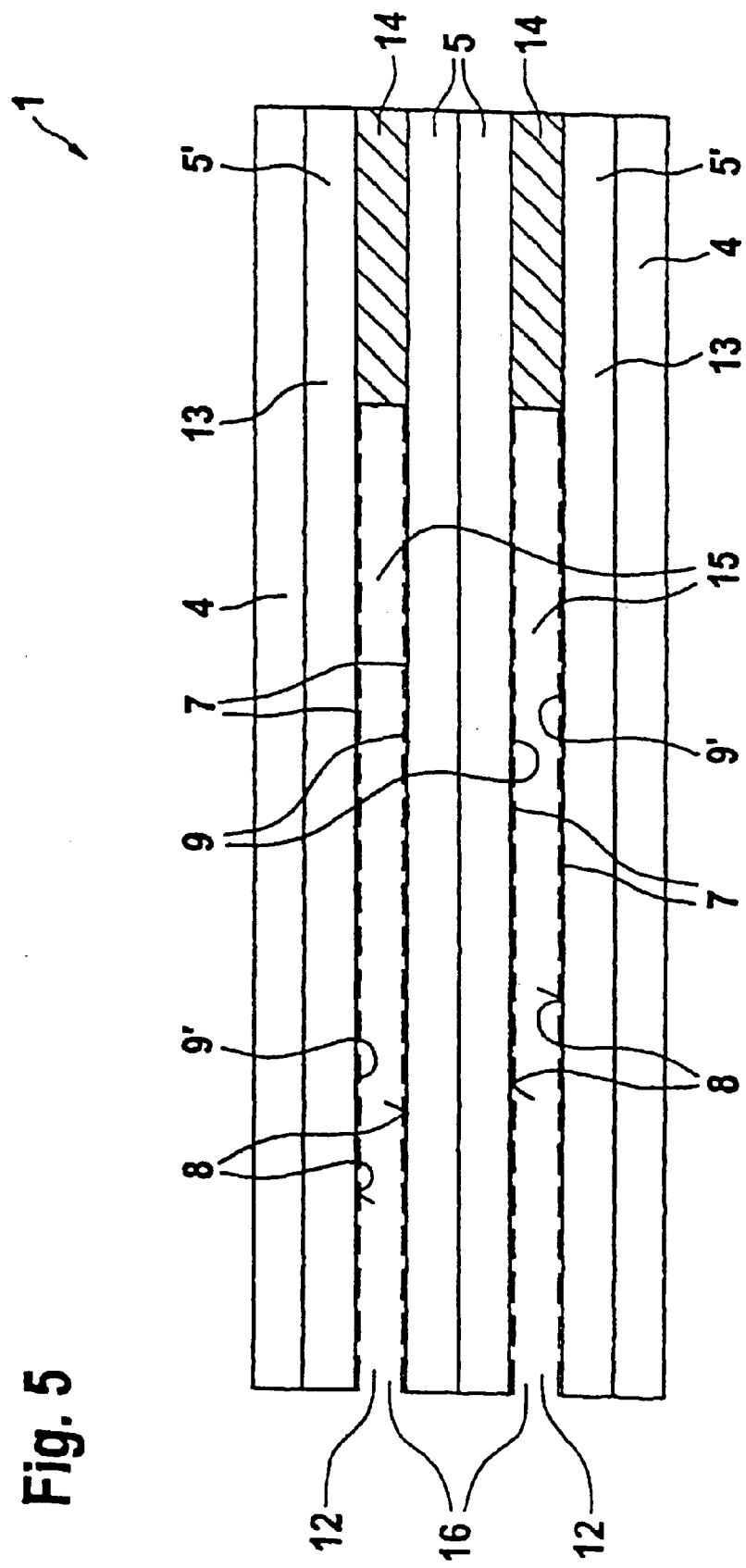
FIG. 5 is a sectional view of a third preferred embodiment of the transducer according to the invention.

FIG. 5 shows a third embodiment of the transducer 1 according to the present invention. In this embodiment the cover plates 13 are configured as further electrode plates 5' with a further diaphragm 9' disposed on a active surface 8 thereof and with a further non-illustrated insulating device 10' disposed in-between. The electrode plates 5 and the further electrode plates 5' are disposed relative to each other in such a way that the diaphragm 9 and the further diaphragm 9' face each other. In the embodiment of FIG. 5 four electrode plates 5, 5', four diaphragms 9, 9', four insulating devices 10, 10' and two support carriers 4 are shown.

We claim:

1. An electrostatic capacitive transducer comprising:
   an electrically conductive fixed electrode plate having an active surface with recesses formed therein;
   a diaphragm, selected from the group consisting of conductive flexible diaphragms and semiconductive flexible diaphragms, disposed at a distance from said active surface of said electrically conductive fixed electrode plate and within said recesses;
   an insulating device disposed between said electrically conductive fixed electrode plate and said diaphragm; and
   a device for detecting a capacitance between said electrically conductive fixed electrode plate and said diaphragm.

2. The transducer according to claim 1, wherein the transducer is an electrostatic electroacoustical transducer for detecting or emitting sound waves.

3. The transducer according to claim 1, wherein the transducer is a sensor for measuring a quantity, which influences a capacitance of the transducer.

4. The transducer according to according to claim 1, wherein said recesses are parallel trenches.

5. The transducer according to claim 4, wherein said trenches have a rectangular cross sectional area.

6. The transducer according to claim 1, wherein said electrically conductive fixed electrode plate and said diaphragm define an air gap there-between functioning as said insulating device.

7. The transducer according to claim 1, wherein said recesses have openings into a back volume of the transducer.

8. The transducer according to claim 7, further comprising a support carrier disposed at a distance from said electrically conductive fixed electrode plate facing a surface of said electrically conductive fixed electrode plate opposite to said active surface, said back volume being delimited by said electrically conductive fixed electrode plate and by said support carrier.

9. The transducer according to claim 1, further comprising a cover plate disposed opposite to said active surface of said electrically conductive fixed electrode plate and at a distance from said diaphragm.

10. The transducer according to claim 9,
    wherein said cover plate is a further electrically conductive fixed electrode plate having a further active surface with further recesses formed therein;
    further comprising a further diaphragm, selected from the group consisting of conductive flexible diaphragms and semiconductive flexible diaphragms, disposed at a distance from said further active surface of the further electrically conductive fixed electrode plate and within said further recesses; and
    further comprising a further insulating device disposed between said further electrically conductive electrode plate and said further diaphragm; and
    wherein said electrically conductive fixed electrode plate and said further electrically conductive electrode plate are disposed relative to each other such that said diaphragm and said further diaphragm face each other.

11. The transducer according to claim 9,
    wherein said electrically conductive fixed electrode plate is one of a plurality of electrically conductive fixed electrode plates;
    wherein said diaphragm is one of a plurality of diaphragms;
    wherein said insulating device is one of a plurality of insulating devices, each of said insulating devices disposed between one of said electrically conductive fixed electrode plates and one of said diaphragms; and
    further comprising a plurality of support carriers, and said electrically conductive fixed electrode plates, said diaphragms, said insulation devices and said support carriers are stacked above each other.

* * * * *

UNITED STATES PATENT AND TRADEMARK OFFICE
CERTIFICATE OF CORRECTION

PATENT NO. : 6,753,583 B2
DATED : June 22, 2004
INVENTOR(S) : Axel Stoffel et al.

It is certified that error appears in the above-identified patent and that said Letters Patent is hereby corrected as shown below:

<u>Title page,</u>
Item [73], Assignee, should read:
-- Fachhochschule Furtwangen, Furtwangen (DE) --.

Signed and Sealed this

Twenty-seventh Day of December, 2005

JON W. DUDAS
*Director of the United States Patent and Trademark Office*